United States Patent [19]

Koskenniska

[11] 4,298,539
[45] Nov. 3, 1981

[54] PROCESS FOR THE ISOLATION OF β-SITOSTEROL

[75] Inventor: Lasse A. Koskenniska, Oulu, Finland

[73] Assignee: Farmos-Yhtma OY, Turku, Finland

[21] Appl. No.: 202,068

[22] Filed: Oct. 30, 1980

[30] Foreign Application Priority Data

Nov. 19, 1979 [FI] Finland .................................. 793612

[51] Int. Cl.$^3$ ............................................... C07J 9/00
[52] U.S. Cl. .................................................. 260/397.25
[58] Field of Search ................................... 260/397.25

[56] References Cited

U.S. PATENT DOCUMENTS

| | | | |
|---|---|---|---|
| 2,839,544 | 6/1958 | Greiner et al. | 260/397.25 |
| 3,691,211 | 9/1972 | Julian | 260/397.25 |
| 4,265,824 | 5/1981 | Koskenniska et al. | 260/397.25 |

Primary Examiner—Elbert L. Roberts
Attorney, Agent, or Firm—J. Harold Nissen

[57] ABSTRACT

A process is provided herein for the isolation and recovery of β-sitosterol substantially free of α-sitosterol from the unsaponifiables obtained from crude soap skimmings or from a crude sterol mixture containing β-sitosterol, α-sitosterol and campesterol. The starting material is treated with a solvent mixture containing an aromatic hydrocarbon, a polar organic solvent having the ability to form hydrogen bonds, and water. The aromatic hydrocarbon can be replaced by a mixture of an aromatic and an aliphatic hydrocarbon. When the starting material is dissolved the reaction product is precipitated, preferably by cooling the solution, whereafter it is separated from the mother liquor. The obtained product is essentially free of α-sitosterol.

8 Claims, No Drawings

PROCESS FOR THE ISOLATION OF β-SITOSTEROL

This invention relates to a process for the isolation of β-sitosterol from mixtures containing in addition to β-sitosterol also other sterols, for example α-sitosterol and campesterol. Such sterol containing mixtures are for example the neutral fraction of the crude soap obtained as by-product in the sulphate cellulose process, the crude sterol mixture obtained from said neutral fraction or a sterol mixture of a different origin, for example from vegetable extractives.

In the pharmaceutical industry β-sitosterol can be used as such for medical use or as a raw material in the manufacture of steroide intermediates. It is, however, of the greatest importance that the β-sitosterol fulfills certain quality demands. It is for instance necessary to obtain a β-sitosterol essentially free of α-sitosterol. The α-sitosterol content must not exceed 4%.

Natural sources of β-sitosterol, such as the crude sterol mixture obtained from the neutral fraction of the crude soap from the sulphate cellulose process, may contain as much as 20% α-sitosterol or even more. Thus, the separation of α- and β-sitosterol, is of utmost practical importance. For the solution of this problem a.o. the following procedures have been proposed:

U.S. Pat. No. 2,573,265 discloses a process for the separation of β-sitosterol and closely related sterols from other sterols, wherein the starting material is dissolved in a hydrocarbon or in a halogenated hydrocarbon, after which the β-sitosterol and like are crystallized with $HClO_4$ or $HPF_6$.

In the publication Sci. Res. (Dakka, Pak.) 1969, p. 162 the separation of α- and β-sitosterol chromatographically on aluminium oxide is described.

The Finnish Patent Application No. 78 3807 discloses a method for the isolation of β-sitosterol from mixtures containing inter alia α-sitosterol. According to this method the starting material is treated with a strong inorganic or organic acid in an organic solvent. The reaction product obtained, which can be separated from the solution for instance by filtration of the cooled solution or by distilling the solvent off, is recrystallized from an organic solvent. If a sterol mixture separated from the neutral fraction of the crude soap is used as starting material, the end product obtained by the use of this method contains about 90% β-sitosterol, about 6% campesterol, isomeres resulting from the decomposition of the α-sitosterol and possibly water splitting products. The end product contains very little pure α-sitosterol; below 2% if proper conditions have been chosen.

The Finnish Patent Application No. 783279 describes a method for the removing of α-sitosterol from β-sitosterol concentrates, wherein the β-sitosterol is treated with a mixture of solvents containing aromatic and/or aliphatic hydrocarbons and esters. In addition to this the mixture may contain small amounts of ketones, alcohols, organic acids and water. A disadvantage of this method is that the β-sitosterol yield remains quite low, below 55%, and that the α-sitosterol content of the end product remains above 2%.

An object of this invention is to eliminate the above mentioned drawbacks. According to the method in this invention, the recovery of β-sitosterol occurs at a high yield, above 70%, if the conditions are properly chosen. In addition to this the α-sitosterol content of the end product is below 2% and at the same time the campesterol content is decreased to some extent, too. This is preferably, when the end product is used for medical purposes. An especially important advantage is that the end product does not practically contain any other harmful components. In addition to campesterol, β- and α-sitosterol, the end product contains only very small amounts of other components, all together they are below 0,5% of the end product.

The process of the present invention is characterized as follows: The starting material, which is a β-sitosterol containing mixture, is refluxed in a solvent mixture containing an aromatic hydrocarbon, preferably an alkylbenzene derivative, a polar organic solvent having the ability to form hydrogen bonds, preferably an alcohol or a ketone, and water. The aromatic hydrocarbon can be replaced by a mixture of an aromatic and an aliphatic hydrocarbon. When the starting material is dissolved, the reaction product is precipitated for example by cooling the solution. The precipitated reaction product contains at most 4% α-sitosterol. If an even lower α-sitosterol content is desired, the method mentioned above can be repeated using the obtained end product as starting material. The solvents used in the process can easily be regenerated by distillation because of their high stability and good volatility.

The invention is described in detail by the following examples. In all the examples a sitosterol mixture isolated from the neutral fraction of the crude soap is used as starting material. The isolation has been performed according to a method disclosed in the U.S. Pat. No. 4,153,622. The composition of the sitosterol mixture used as starting material has been as follows:

| β-sitosterol | 64,8% |
|---|---|
| α-sitosterol | 19,0% |
| campesterol | 5,5% |
| others | 10,7% |

The invention is of course not restricted to the above mentioned starting material. Other β-sitosterol containing mixtures with impurities of α-sitosterol can be used as well. Such sterol mixtures are for example the neutral fraction of the crude soap from the sulphate cellulose process, neutral extractives obtained from soya, wheat, sugar cane etc. and tall oil pitch.

EXAMPLE 1

5,0 of crude β-sitosterol was weighed into a reaction flask. 20 ml of heptane, 10 ml of xylene, 5 ml of methanol and 1 ml of water were added. The mixture was refluxed until the starting material was dissolved. The mixture was then cooled to +5° C. −0° C. The mixture was kept in this temperature range for 4 h. The precipitation was filtered off giving 2,8 g product of the following composition:

| β-sitosterol | 93,4% |
|---|---|
| campesterol | 4,9% |
| α-sitosterol | 1,4% |
| others | 0,3% |

EXAMPLE 2

5,0 g of crude β-sitosterol was weighed into a reaction flask. 15 ml of heptane, 10 ml of mesitylene, 10 ml of methanol and 1 ml of water were added. The procedure of the previous example was repeated giving 2,5 g product of the following composition:

| β-sitosterol | 94,3% |
|---|---|
| campesterol | 4,8% |
| α-sitosterol | 0,8% |
| others | 0,1% |

EXAMPLE 3

5,0 g of crude β-sitosterol was weighed into a reaction flask. 20 ml of hexane, 10 ml of toluene, 5 ml of ethanol and 1 ml of water were added. The procedure of example 1 was repeated giving 2,2 g product of the following composition:

| β-sitosterol | 92,5% |
|---|---|
| campesterol | 5,1% |
| α-sitosterol | 2,0% |
| others | 0,4% |

EXAMPLE 4

5,0 g of crude β-sitosterol was weighed into a reaction flask. 20 ml of heptane, 10 ml of xylene, 5 ml of ethanol and 1 ml of water were added. The procedure of example 1 was repeated except that the mixture was cooled to +15° C. 1,6 g product was obtained and it had the following composition:

| β-sitosterol | 94,0% |
|---|---|
| campesterol | 4,8% |
| α-sitosterol | 1,1% |
| others | 0,1% |

EXAMPLE 5

5,0 g of crude β-sitosterol was weighed into a reaction flask. 20 ml of xylene, 15 ml of methylene chloride and 2 ml of water were added. The procedure of example 1 was repeated giving 2,2 g product of the following composition:

| β-sitosterol | 92,4% |
|---|---|
| campesterol | 5,1% |
| α-sitosterol | 2,0% |
| others | 0,5% |

EXAMPLE 6

5,0 of crude β-sitosterol was weighed into a reaction flask. 20 ml of toluene, 15 ml of acetone and 2 ml of water were added. The procedure of example 1 was repeated giving 2,5 g product of the following composition:

| β-sitosterol | 93,3% |
|---|---|
| campesterol | 4,9% |
| α-sitosterol | 1,5% |
| others | 0,3% |

EXAMPLE 7

5,0 g of crude β-sitosterol was weighed into a reaction flask. 20 ml of xylene, 15 ml of acetone and 2 ml of water were added. The procedure of example 1 was repeated giving 2,6 g product of the following composition:

| β-sitosterol | 94,0% |
|---|---|
| campesterol | 4,9% |
| α-sitosterol | 1,1% |
| others | 0,0% |

The method is easily applicable in industrial scale as a batch process. The starting material (a β-sitosterol containing mixture) and the mixture of the solvents are added to the reactor and refluxed until the starting material is dissolved. The solution is cooled to 0°–+5° C., where it is kept for 4 h. After this the precipitation is filtered off. A white product is obtained at a yield of 76–96% depending on the α-sitosterol content of the starting material. The α-sitosterol content of the end product is about 3% if the α-sitosterol content of the starting material has been 20–25%. The α-sitosterol content of the end product can be decreased by raising the cooling temperature.

The mixture of the organic solvents are distilled off from the mother liquor. Water is added to the residue. Then the mixture containing α-sitosterol, campesterol and other neutral impurities is filtered off. The α-sitosterol content in the residue is 60–62% (packed column SE-30).

If desirable the process is repeated using the end product as starting material. The operation is carried out at the same solvent ratios. This results in a β-sitosterol product containing less than 1% α-sitosterol.

I claim:

1. A method for the isolation of β-sitosterol essentially free of α-sitosterol from a mixture containing both α- and β-sitosterol by treating the said mixture with a mixture of organic solvents and water wherein
    (a) the solvent mixture is added to the β-sitosterol containing starting material so that the weight ratio of β-sitosterol containing starting material: solvent mixture is 1:2–1:30, and the solvent mixture consists of
        a hydrocarbon selected from the class consisting of a single aromatic hydrocarbon and a mixture of an aromatic and an aliphatic hydrocarbon, in an amount of 10–99%,
        a polar organic solvent, 1–90% water, at least in an amount necessary to saturate the hydrocarbon layer
    (b) the mixture is warmed until the β-sitosterol containing starting material is dissolved
    (c) the product is precipitated,
    (d) the precipitate, which is essentially free of α-sitosterol is separated from the mother liquor by filtration.

2. A method according to claim 1, wherein the polar solvent used has the ability to form hydrogen bonds.

3. A method according to claim 2, wherein a lower alcohol is used as the polar solvent.

4. A method according to claim 2, wherein a lower ketone is used as the polar solvent.

5. A method according to claim 1, wherein the steps a–d are repeated using the end product from step d as starting material.

6. A method according to claim 1, wherein the precipitation in step c is performed by cooling the mixture.

7. A method according to claim 1, wherein the weight ratio of β-sitosterol containing starting material: solvent mixture is 1:5–1:8.

8. A method according to claim 1, wherein the solvent mixture consists of
   a hydrocarbon selected from the class consisting of a single aromatic hydrocarbon and a mixture of an aromatic and aliphatic hydrocarbon, 40–85%
   a polar organic solvent 10–55%
   water, at least in an amount necessary to saturate the hydrocarbon layer.

* * * * *